United States Patent [19]

Willis et al.

[11] Patent Number: 4,605,778
[45] Date of Patent: Aug. 12, 1986

[54] PROCESS FOR THE PREPARATION OF AROMATIC MUSKS

[75] Inventors: Brian J. Willis, Ramsey, N.J.; Teodosij Zazula, Rego Park, N.Y.

[73] Assignee: Fritzsche Dodge & Olcott Inc., New York, N.Y.

[21] Appl. No.: 617,990

[22] Filed: Jun. 6, 1984

Related U.S. Application Data

[60] Division of Ser. No. 494,674, May 13, 1983, Pat. No. 4,476,040, which is a continuation-in-part of Ser. No. 394,847, Jul. 2, 1982, abandoned.

[51] Int. Cl.$^4$ .................... C07C 45/00; C07C 45/90
[52] U.S. Cl. .................... 568/433; 568/426; 568/633
[58] Field of Search .................... 568/426, 433, 630

[56] References Cited

U.S. PATENT DOCUMENTS

| | | | |
|---|---|---|---|
| 675,543 | 6/1901 | Eichengrün | 568/433 |
| 1,345,649 | 7/1920 | Weiss | 568/433 |
| 2,450,877 | 10/1948 | Carpenter et al. | 568/426 |
| 2,516,412 | 7/1950 | Pearl | 568/426 |
| 2,683,748 | 7/1954 | Bell | 568/630 |
| 2,775,613 | 12/1956 | Garber | 568/433 X |
| 3,867,458 | 2/1975 | Imai et al. | 568/433 |
| 3,987,105 | 10/1976 | Yardley | 568/433 |
| 4,064,349 | 12/1977 | Papenfuhs | 560/56 |
| 4,151,201 | 4/1979 | Casnati et al. | 568/426 |
| 4,153,810 | 5/1979 | Neumann et al. | 568/630 |
| 4,169,108 | 9/1979 | Bailey | 568/433 X |
| 4,192,949 | 3/1980 | Merger et al. | 568/630 X |
| 4,205,188 | 5/1980 | Muench et al. | 568/426 X |
| 4,231,967 | 11/1980 | Matsuda et al. | 568/433 |
| 4,254,276 | 3/1981 | Iori et al. | 568/630 |
| 4,268,444 | 5/1981 | Jaedicke | 568/433 |
| 4,453,004 | 6/1984 | Nelson | 568/433 |
| 4,453,017 | 6/1984 | Nelson | 568/433 |

OTHER PUBLICATIONS

Wagner et al, Synthetic Organic Chem., John Wiley, pp. 226–252 (1965).
Patai, The Chemistry of the Ether Linkage, Interscience, pp. 445–498 (1967).
Barton et al, Comprehensive Organic Chemistry Pergamon, vol. 6, p. 908 (1979).
Patai, The Chemistry of the Carbonyl Group, Interscience, pp. 233–302 (1966).

Primary Examiner—Helen M. S. Sneed
Attorney, Agent, or Firm—Cooper, Dunham, Clark, Griffin & Moran

[57] ABSTRACT

The present invention relates to novel musk compounds, useful as fragrance materials which have the structure:

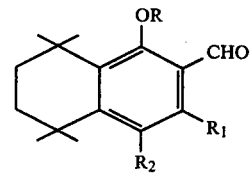

wherein R is hydrogen or methyl and $R_1$ and $R_2$ are hydrogen, methyl, or ethyl, and provides methods for preparing these compounds from readily available intermediates. The invention also provides fragrance compositions which include the compounds, and processes for altering the organoleptic properties of perfume compositions, colognes and perfumed articles by adding organoleptically effective amounts of the compounds.

10 Claims, 15 Drawing Figures

IR SPECTRUM FOR COMPOUND 4a.

IR SPECTRUM FOR COMPOUND 3b.

$^1$H-NMR SPECTRUM FOR COMPOUND 3c.

PROCESS FOR THE PREPARATION OF AROMATIC MUSKS

This is a division of application Ser. No. 494,674, filed May 13, 1983 now U.S. Pat. No. 4,476,040 which is a continuation-in-part of application Ser. No. 394,847 filed July 2, 1982, now abandoned.

The present invention relates to novel aromatic musk compounds represented by the structure:

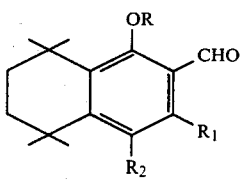

wherein R is methyl or hydrogen and $R_1$ and $R_2$ are hydrogen, methyl, or ethyl, prepared according to the novel processes of this invention, and to the methods in which the compounds of this invention are used to alter, modify, enhance, or improve the organoleptic properties of fragrance compositions and of perfumed articles.

BACKGROUND OF THE INVENTION

Natural sources of musk and musk-like odor have been prized by perfumers for centuries. The limited availability of the natural materials has encouraged a search for inexpensive, more readily available synthetics with musk-like odor. The nitromusks were introduced in the late nineteenth century and much later synthetic musks which did not contain the nitro-function began to appear. Review articles by T. F. Wood in *Givaudanian* between 1968 and 1970 adumbrate the early search for synthetics with musk-like odor. Several of the synthetics mentioned in these articles have found large scale usage by the fragrance industry. However, the safety of certain nitromusks used in large quantities in fragrance compositions has been questioned. Consequently, there is a potential need for new synthetic musks which: may be used as replacements for the nitromusks, can be produced in an economic and straightforward manner, and are toxicologically safe. Such chemicals may be used in the duplication of fragrance notes, as well as in the creation of entirely new fragrance effects.

The review by T. F. Wood (see *Givaudanian*, September 1968, pp 6-7) discloses four tetralin derivatives which are present in Table 1. These compounds are described as nonmusks, and are either odorless or nearly odorless. The organoleptic properties of the compounds of the present invention are completely different from those of the compounds disclosed in the Wood article, since unexpectedly they generally exhibit musk odor. Nowhere in the prior art is there any reference to the compounds of the present invention, or any mention of their organoleptic properties.

TABLE 1

Prior art compounds disclosed in Givaudanian, September 1968, pp 6-7 and their odor descriptions are presented.

| STRUCTURE | ODOR DESCRIPTION |
|---|---|
| [tetralin with COCH₃ and OCH₃ substituents] | Nearly odorless. Devoid of musk odor. |
| [tetralin with CHO and OCH₃ substituents] | Odorless. Nonmusk. |
| [tetralin with OCH₃ and CHO substituents] | Odorless. Nonmusk. |
| [tetralin with OCH₃ and COCH₃ substituents] | Practically odorless. |

BRIEF DESCRIPTION OF THE DRAWINGS

FIG. 1. Illustrates the $^1$H-NMR spectrum of the inventive compound 3a.

FIG. 2. Illustrates the $^{13}$C-NMR spectrum of the inventive compound 3a.

FIG. 3. Illustrates the Infrared spectrum of the inventive compound 3a.

FIG. 4. Illustrates the $^1$H-NMR spectrum of the inventive compound 4a.

FIG. 5. Illustrates the $^{13}$C-NMR spectrum of the inventive compound 4a.

FIG. 6. Illustrates the Infrared spectrum of the inventive compound 4a.

THE INVENTION

Figure 1:
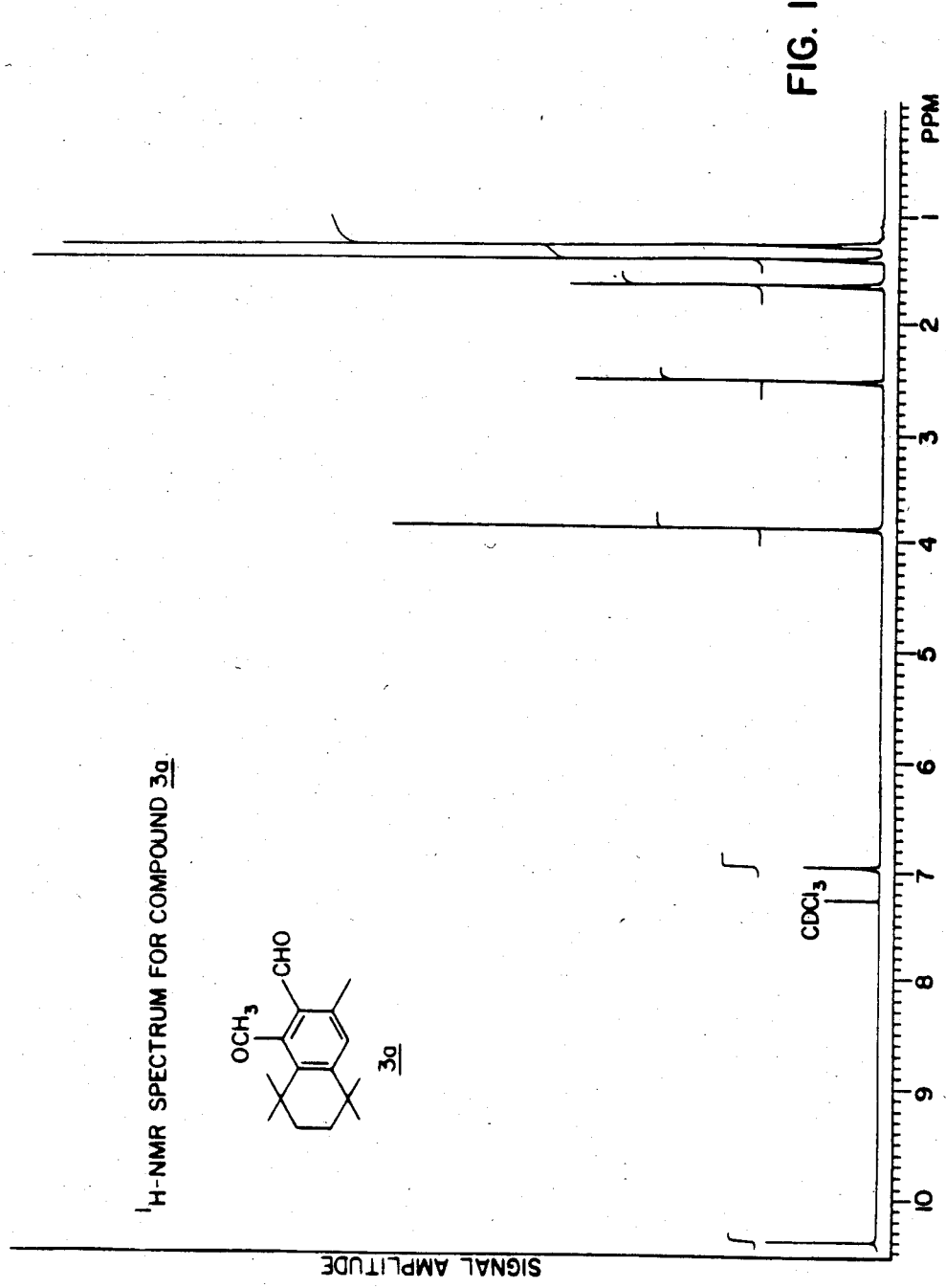
Figure 2:
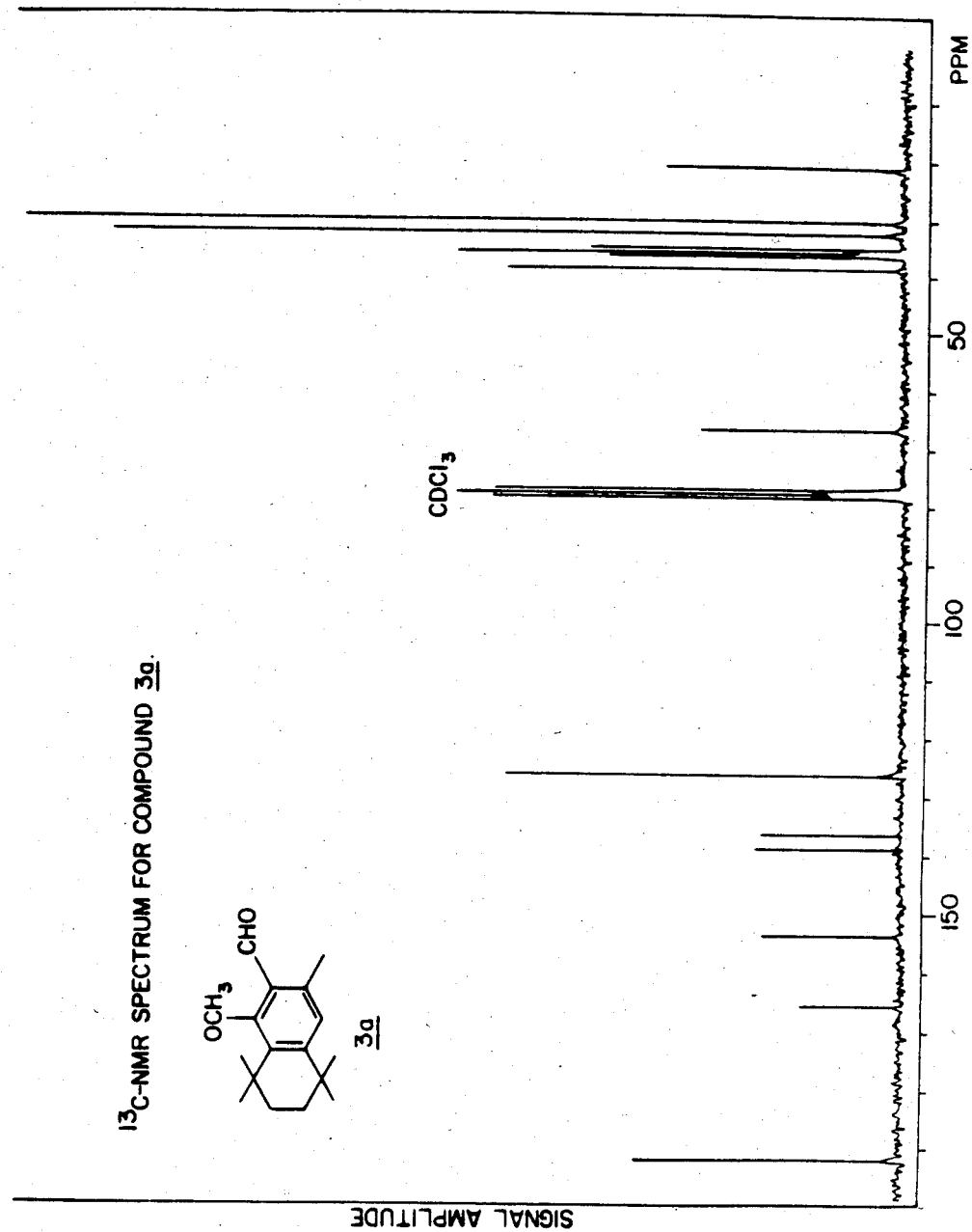
Figure 3:
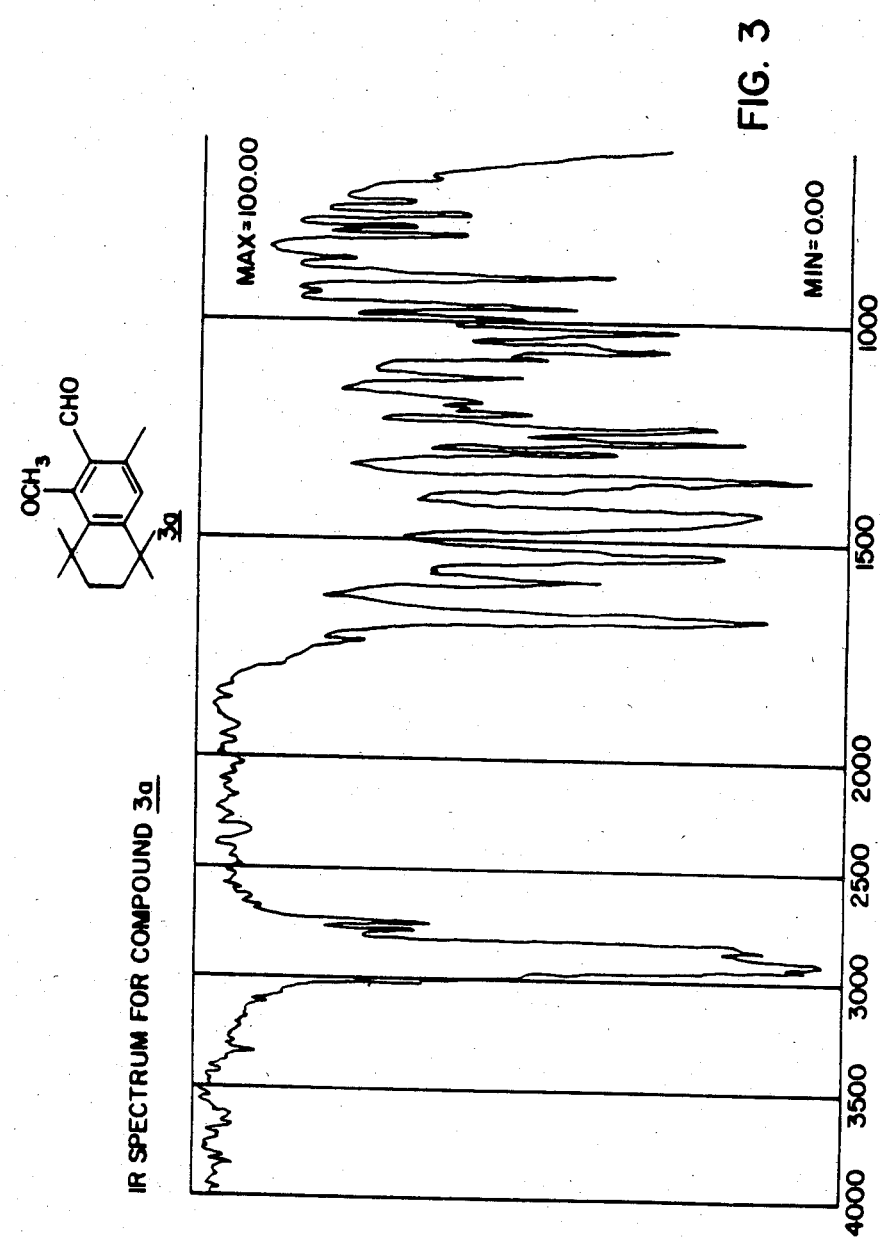
Figure 4:
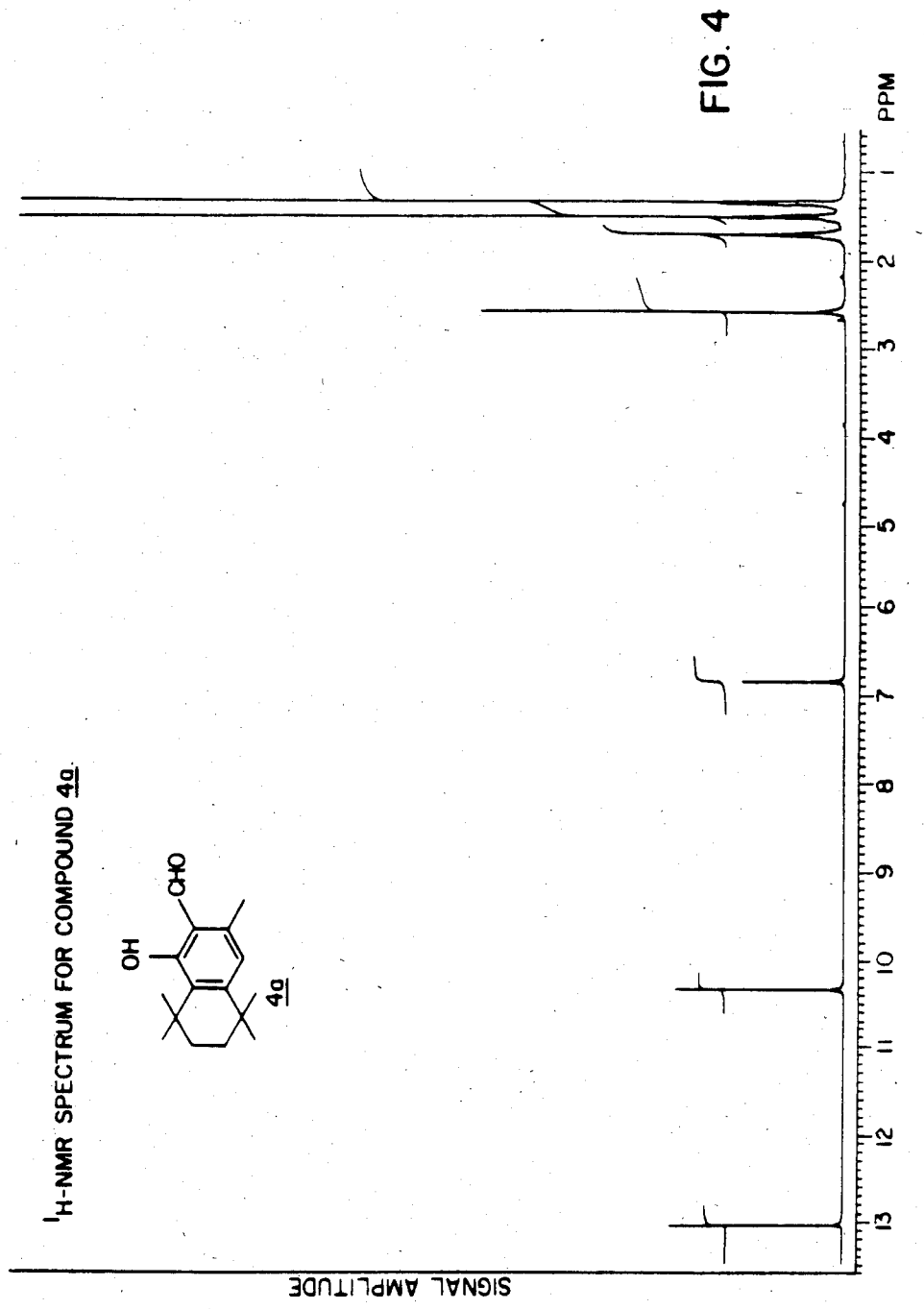
Figure 5:
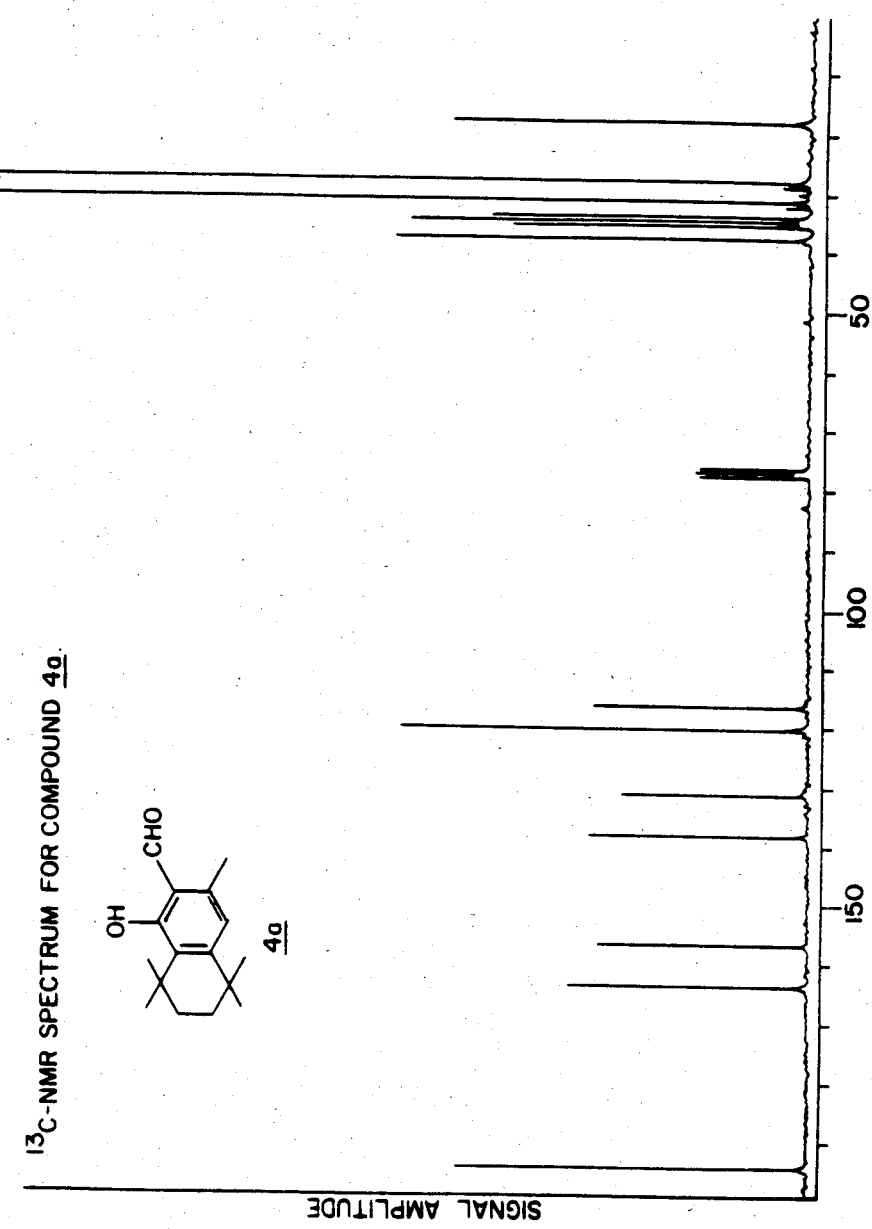
Figure 6:
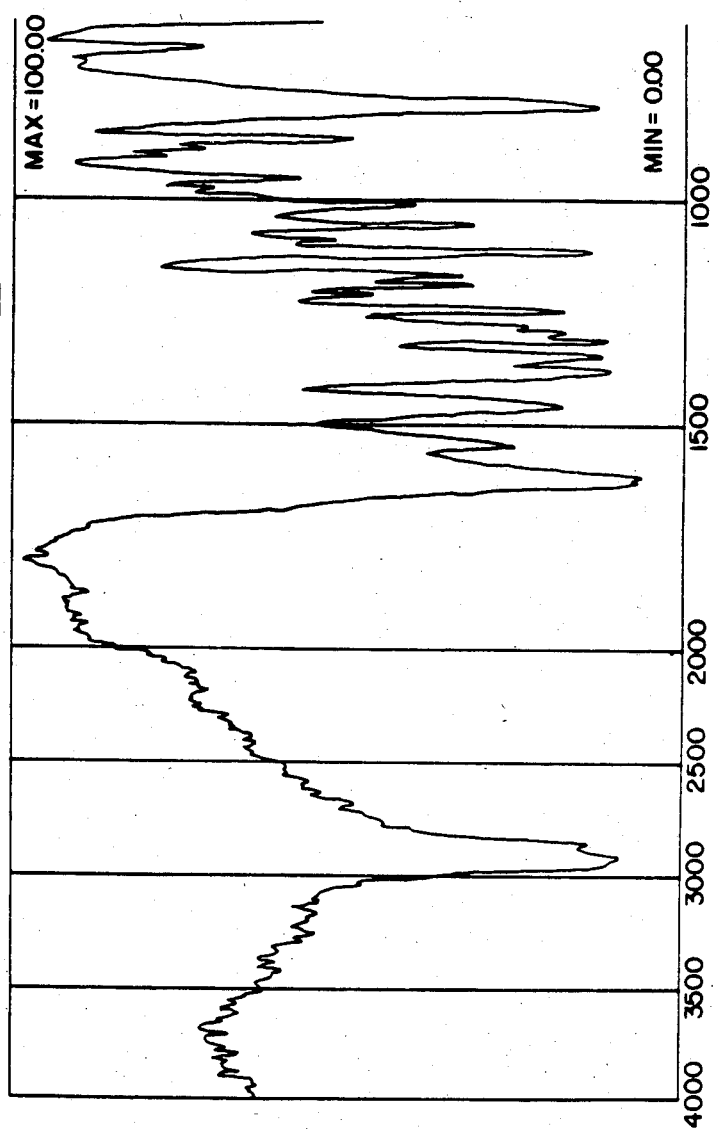
Figure 7:
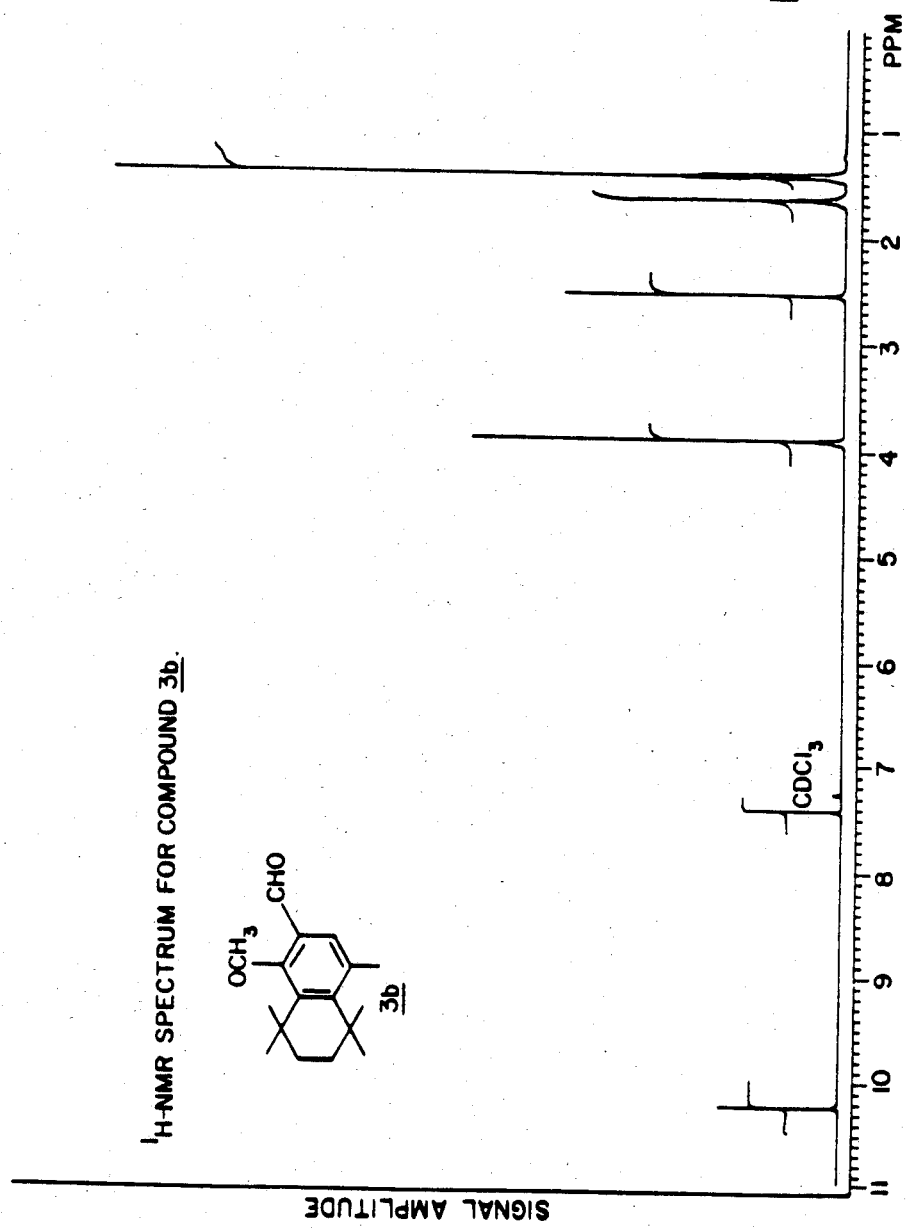
FIG. 7. Illustrates the $^1$H-NMR spectrum of the inventive compound 3b.
Figure 8:
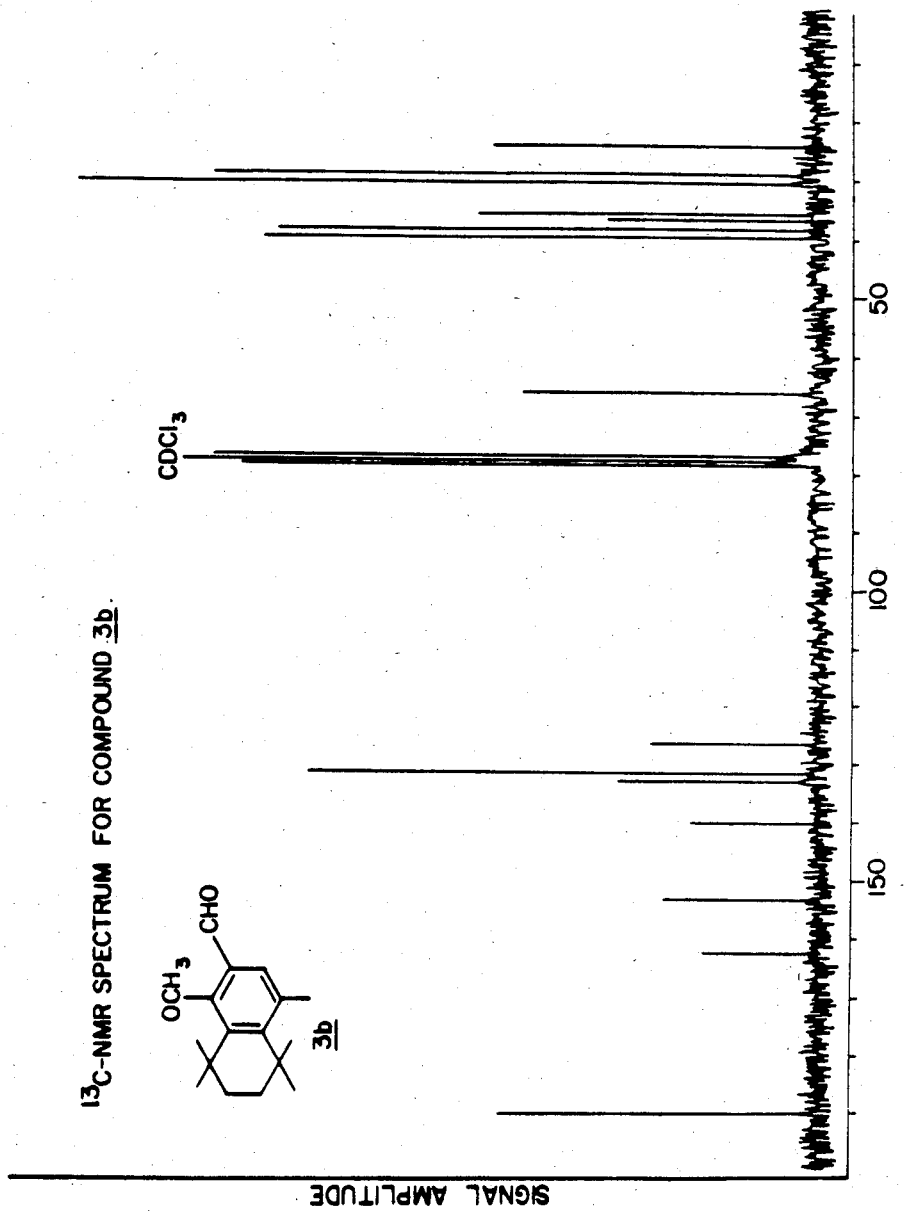
FIG. 8. Illustrates the $^{13}$C-NMR spectrum of the inventive compound 3b.
Figure 9:
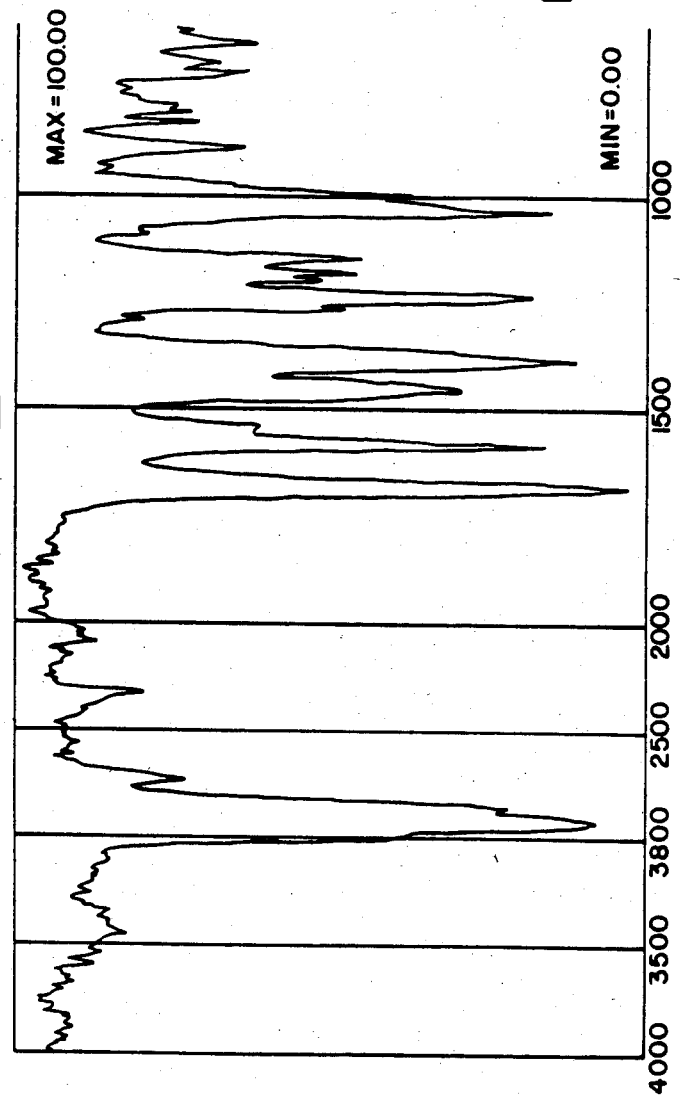
FIG. 9. Illustrates the Infrared spectrum of the inventive compound 3b.
Figure 10:
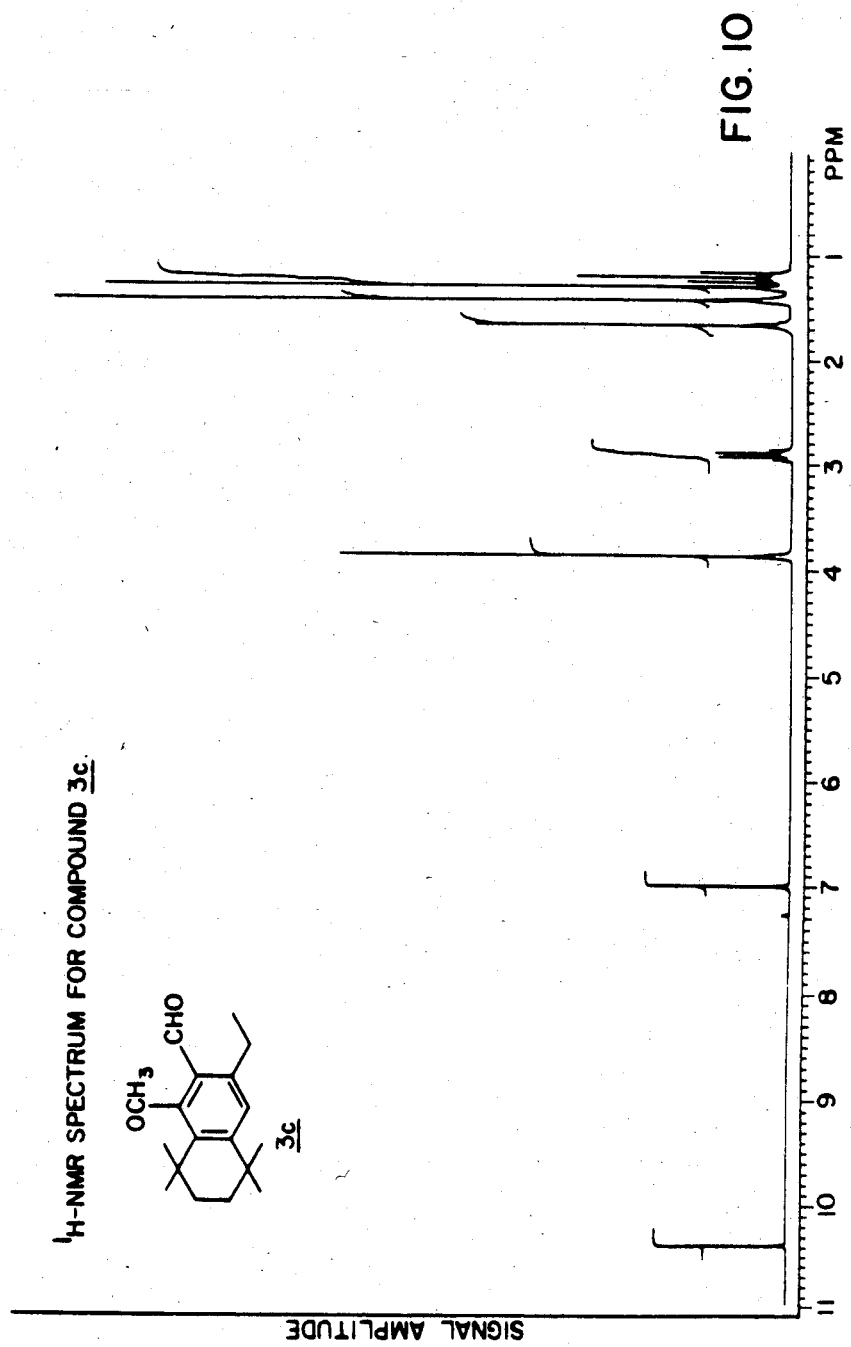
FIG. 10. Illustrates the $^1$H-NMR spectrum of the inventive compound 3c.
Figure 11:
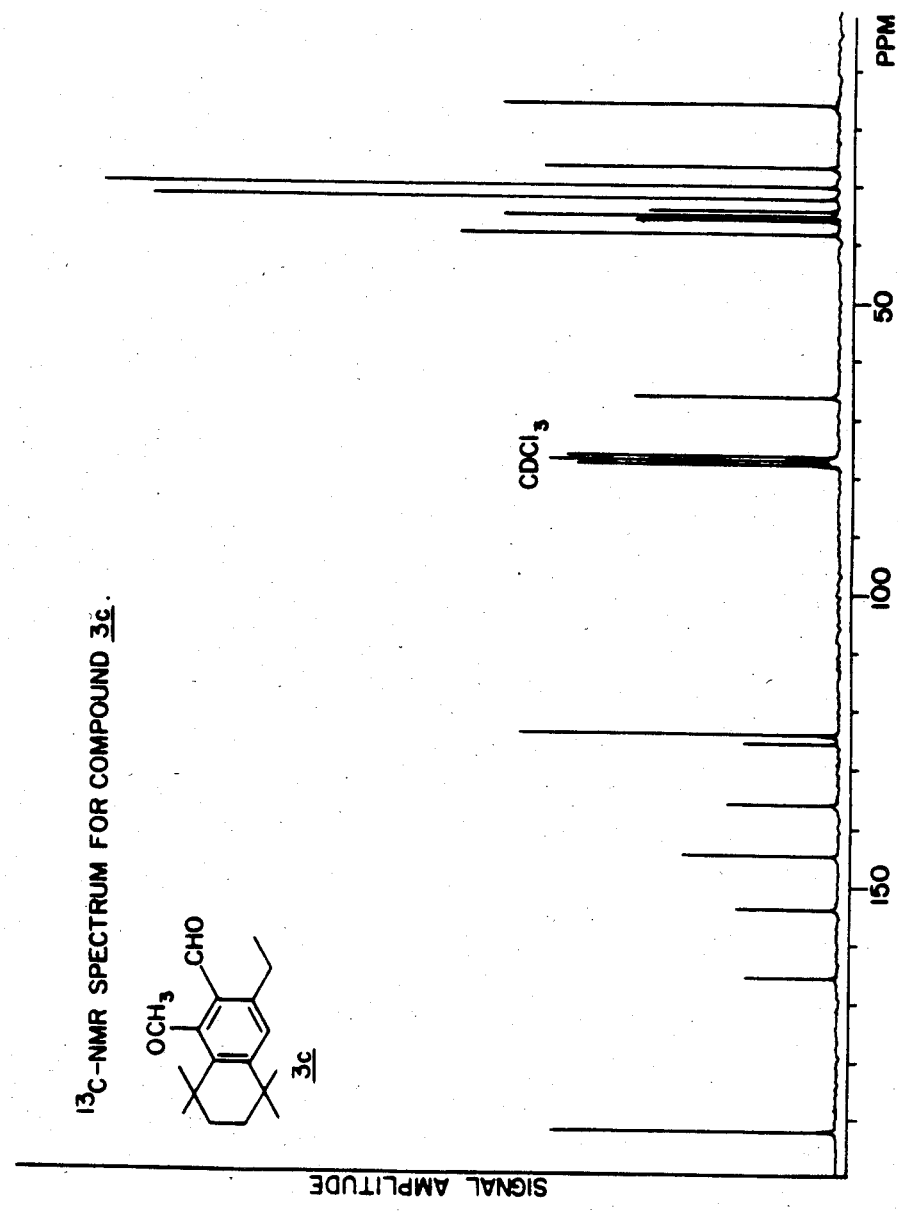
FIG. 11. Illustrates the $^{13}$C-NMR spectrum of the inventive compound 3c.
Figure 12:
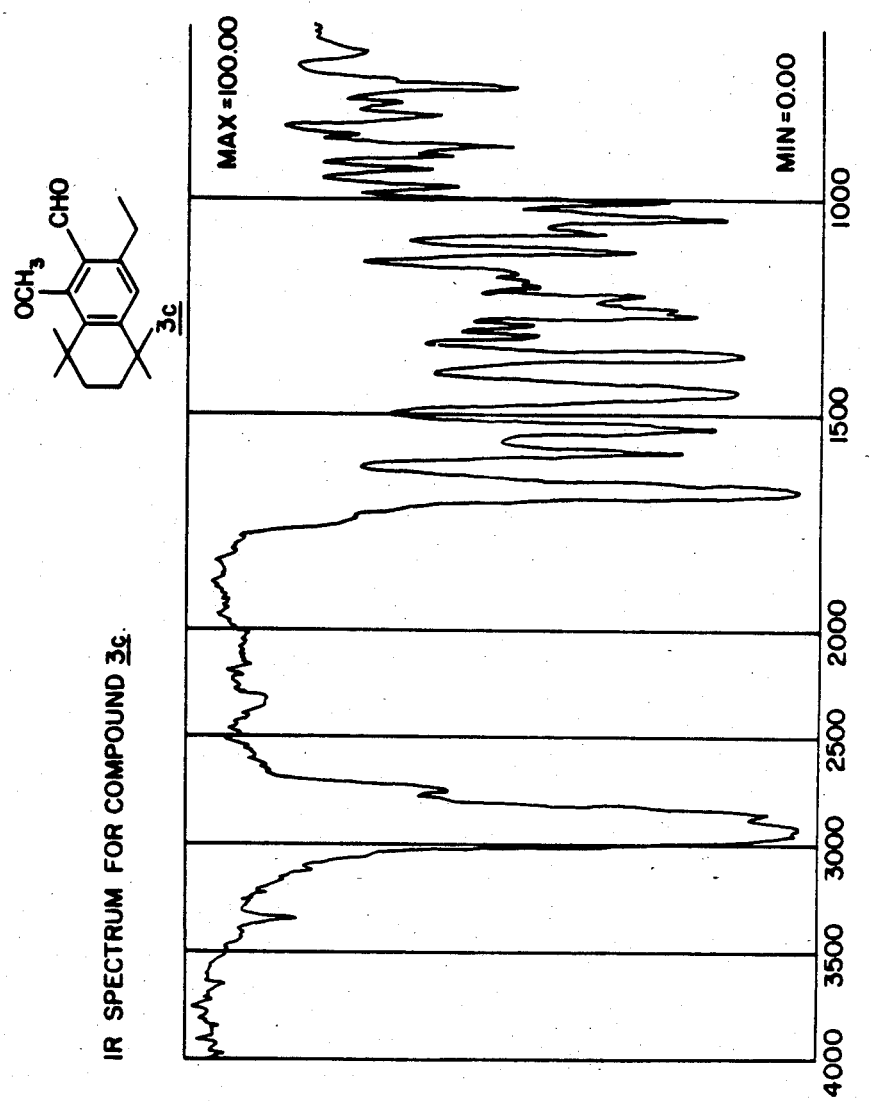
FIG. 12. Illustrates the Infrared spectrum of the inventive compound 3c.
Figure 13:
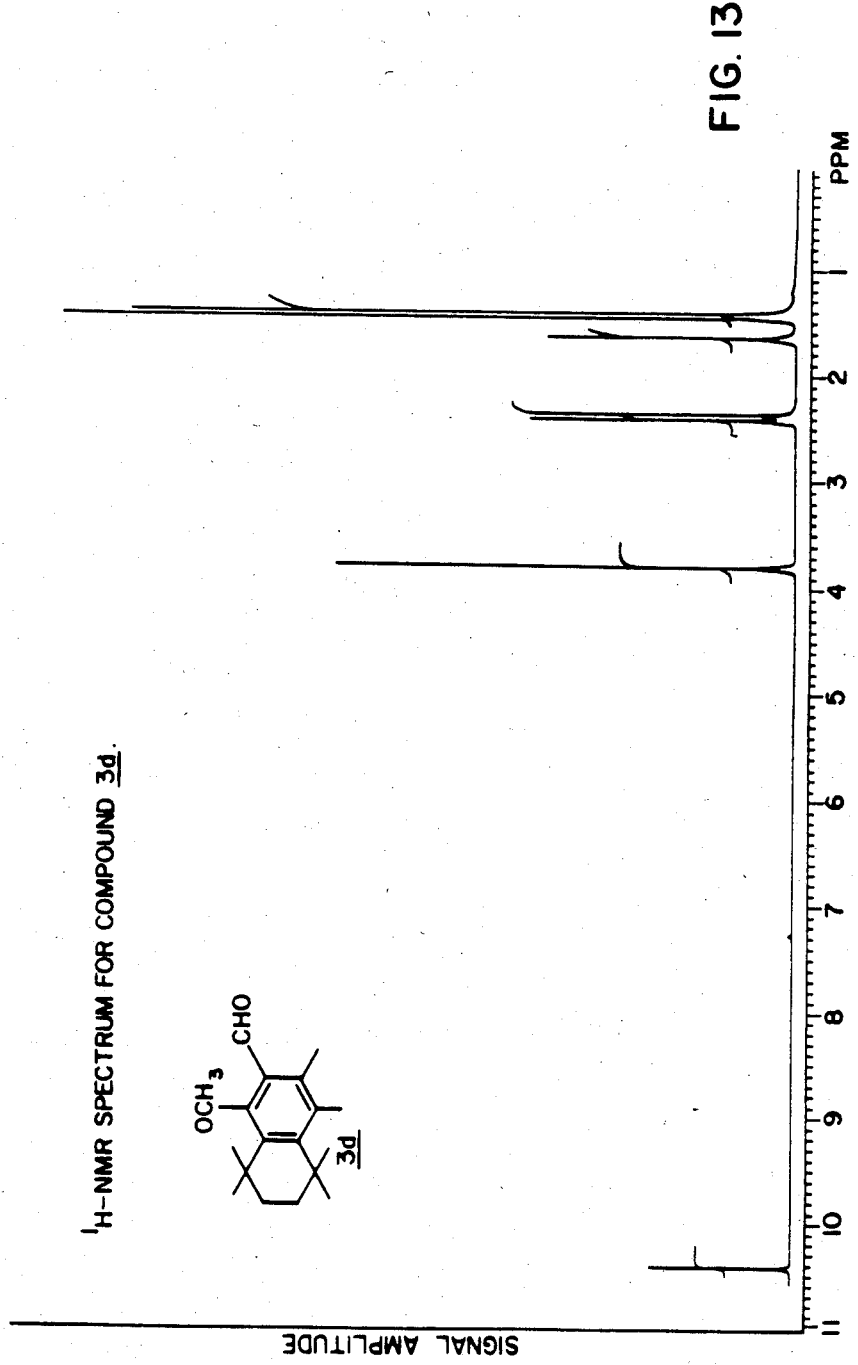
FIG. 13. Illustrates the $^1$H-NMR spectrum of the inventive compound 3d.
Figure 14:
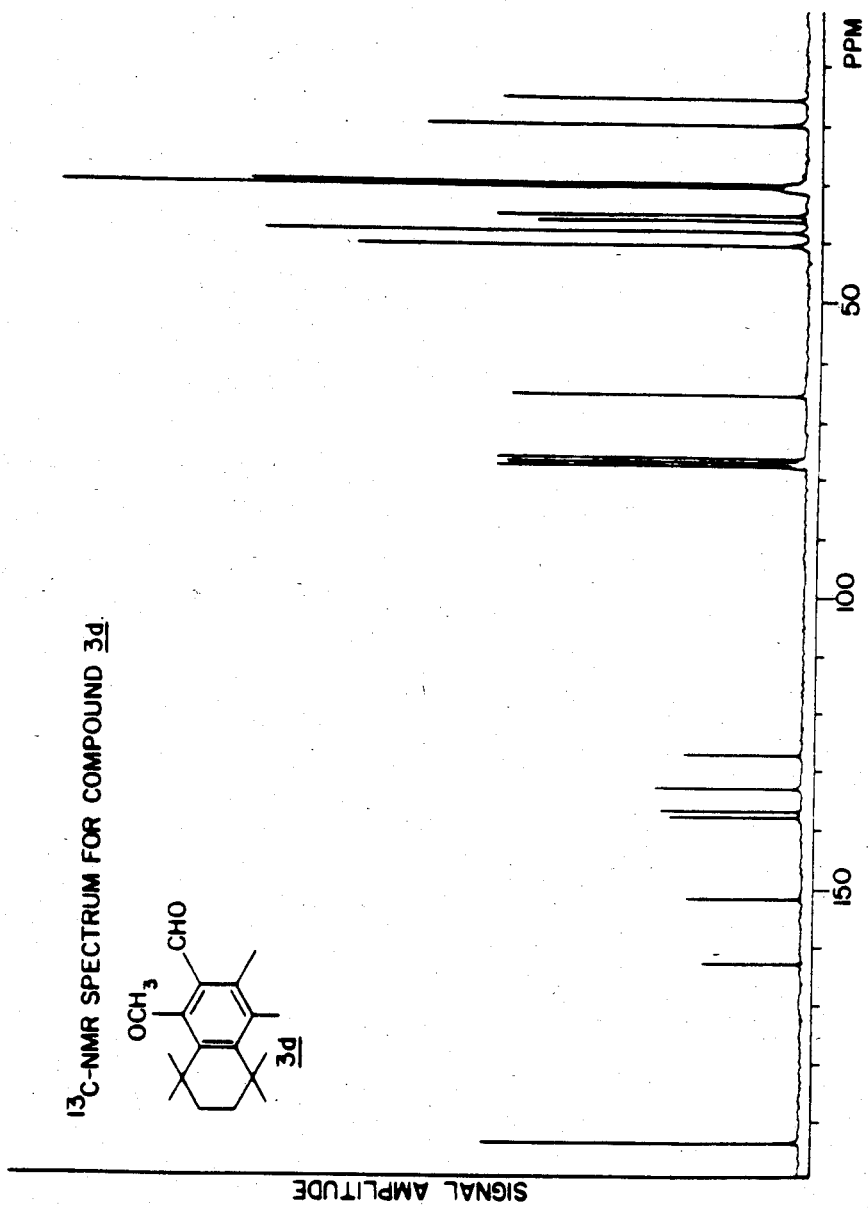
FIG. 14. Illustrates the $^{13}$C-NMR spectrum of the inventive compound 3d.
Figure 15:
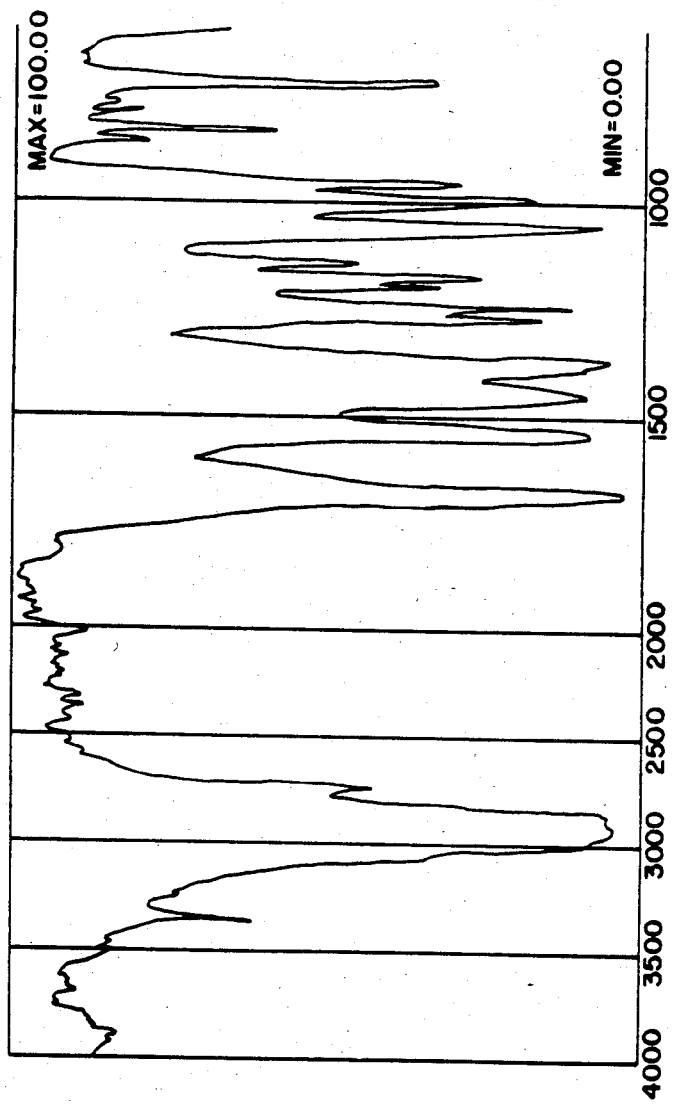
FIG. 15. Illustrates the Infrared spectrum of the inventive compound 3d.

It has been unexpectedly discovered that the compounds having the structure:

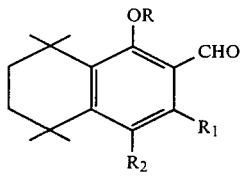

wherein R is hydrogen or methyl and $R_1$ and $R_2$ are hydrogen, methyl or ethyl exhibit musk odor, often with a woody and sweet note.

Examples of some of the inventive compounds and their odor descriptions are presented in Table 2.

TABLE 2

| INVENTIVE STRUCTURES | ODOR DESCRIPTION |
|---|---|
| 3a | Strong and excellent musk. Close in character to Musk Ambrette, but finer, sweeter, and more powerful. Exalting, with the character of the macrocyclic musks. |
| 3b | Low-odored musk, woody and slightly sweet. |
| 3c | A sweet, exalting musk with a woody nuance. |
| 3d | Low-keyed musk, slightly sweet and woody. |
| 4a | Strong sweet musk with a rich woody nuance. |

The inventive compounds 3 and 4, where R is hydrogen or methyl and $R_1$ and $R_2$ are hydrogen, methyl or ethyl, may be prepared from a substituted tetrahydronaphthalene 1, wherein $R_1$ and $R_2$ are hydrogen, methyl or ethyl. The following reaction scheme illustrates two processes for conveniently and inexpensively preparing the compounds 3 and 4 of this invention from Compound 1.

The inventive compounds may be prepared by formylation, or formylation and methylation of the appropriate substituted tetrahydronaphthalene 1. The order of formylation and methylation is not critical, i.e. the substituted tetrahydronaphthalene 1 may first be formylated and then methylated, or vise-versa.

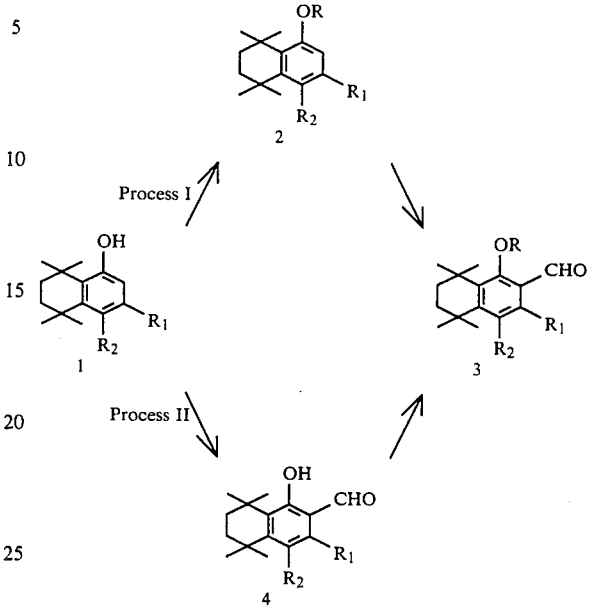

PROCESS I comprises: (a) methylation of Compound 1 to produce a substituted tetrahydronaphthalene 2, (b) formylation of Compound 2 to produce Compound 3, and (c) recovery of Compound 3.

PROCESS II comprises: (a) formylation of Compound 1 to produce a substituted tetrahydronaphthalene 4, (b) methylation of Compound 4 to product Compound 3, and (c) recovery of Compound 3.

The Compound 4 is prepared by an abridged version of Process II which comprises: (a) formylation of Compound 1 to produce Compound 4; and (b) recovery of Compound 4.

The methylation reaction employed in either process may be accomplished in a variety of ways according to well-known techniques. Such techniques are exemplified in R. B. Wagner and H. D. Zook "Synthetic Organic Chemistry", John Wiley, 1965, pp 226-252, and "The Chemistry of the Ether Linkage", Ed. S. Patai, Interscience, 1967, pp 445-498, which are incorporated herein by reference. Similarly, the formylation reaction may be accomplished in a variety of ways according to well-known techniques. Such techniques are exemplified in "Comprehensive Organic Chemistry", Pergamon, Ed. D. H. R. Barton and W. D. Ollis, 1979, Vol. 6, p 908, and "The Chemistry of the Carbonyl Group", Ed. S. Patai, Interscience, 1966, pp 233-302, which are incorporated herein by reference. Isolation and purification of the final products is achieved by conventional techniques including extraction, distillation, crystallization and the like.

On the basis of their valuable olfactory properties, the inventive compounds have been found to be suitable for use in fine fragrance compositions, as well as in perfumed products, such as soaps, detergents, deodorants, cosmetic preparations and the like. Such fragrance compositions may comprise an organoleptically effective amount of one or more of the novel compounds and at least one other organoleptic agent.

The term "organoleptically effective amount" is used herein to mean a level or amount of compound present in a perfume composition or perfumed article at which the incorporated compound(s) exhibit(s) a sensory effect.

Perfume compositions are carefully balanced, harmonious blends of essential oils, aroma chemicals, resinoids and other extracts of natural odorous materials. Each ingredient imparts its own characteristic effect to the composition. However, the overall sensory effect of the perfume composition will be at least the sum total of the effects of each of the ingredients. One or more of the novel tetrahydronaphthalene derivatives of this invention can be used to alter, modify or enhance the aroma characteristics of a perfume composition, for example, by utilizing or moderating the olfactory reaction contributed by another ingredient in the composition.

The terms "alter" and "modify" are used herein to mean supply or impart an aroma character or note to otherwise relatively odorless substances, or augment the existing fragrance characteristics of a composition which is deficient in some regard, or to supplement the existing fragrance or aroma impression to modify its quality, character or odor. The term "enhance" is used herein to mean the amplification or intensification of the quality thereof.

The amount of tetrahydronaphthalene derivative(s) of our invention which will be effective in perfume compositions as well as in perfumed articles and colognes depends on many factors. Such factors include the other ingredients in the composition or article, their concentrations, and the overall sensory effect desired. The tetrahydronaphthalene derivative(s) can be used in amounts of as little as 0.01% and often as low as 0.0001% to impart significant odor characteristics to perfumed articles, e.g. soaps, detergents, cosmetics, fabric softener compositions or articles, and other products. The amount employed can range up to about 80% of the fragrance components and up to about 7.0% of the quantity of perfumed article and will depend on considerations of cost, nature of the end product, the effect desired on the finished product, and the particular fragrance sought.

The tetrahydronaphthalene derivative(s) of our invention may be used alone or in combination with other ingredients in perfume compositions or as (an) olfactory component(s) in lacquers, brilliantines, pomades, shampoos, cosmetic preparations, powders and the like. When used as (an) olfactory component(s) as little as 0.0001% of tetrahydronaphthalene derivative(s), more preferably 1.0%, (based on weight of perfume composition) will suffice to impart a significant odor characteristic. Generally, no more than 7.0% of tetrahydronaphthalene derivative(s) based on the ultimate end-product is required in the perfume composition. Furthermore, the novel tetrahydronaphthalene derivative(s) may be employed in such a manner to provide a method for modifying, enhancing or improving the organoleptic properties of perfume compositions, colognes and perfumed articles by adding thereto an organoleptically effective amount of the novel chemicals of this invention.

The following examples are set forth herein to illustrate methods of synthesis of the compounds of this invention and their use in fragrance compositions. These examples are intended only to illustrate the embodiments of this invention and are in no way meant to limit the scope thereof.

EXAMPLE 1

This example provides a method for producing 1-hydroxy-3,5,5,8,8-pentamethyl-5,6,7,8-tetrahydronaphthalene. The method is illustrated by the following reaction sequence:

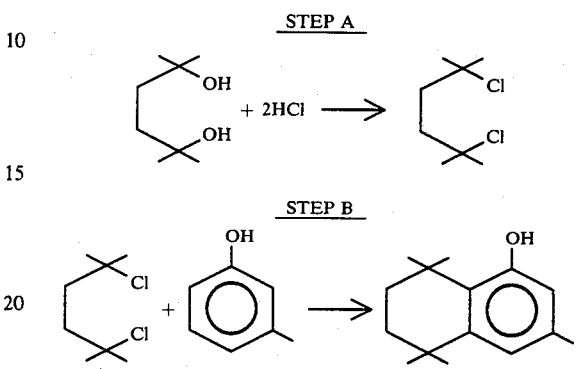

STEP A. Concentrated hydrochloric acid (8,260 g, 86 mol) was added in one portion to 2,5-dimethyl-2,5-hexane diol (4,478 g, 46.65 mol). The resulting solution was heated for 6 h, with stirring at 22°–75° C., while passing hydrogen chloride gas (200 g). Then the reaction mixture was cooled to 25° C., hexane (3.5 L) added, and the mixture stirred vigorously. The organic layer was separated, washed with water (2×1 L), neutralized with 5% sodium bicarbonate solution and dried ($Na_2SO_4$). The solvent was removed by distillation and the residue was crystallized from hexane to give 2,5-dimethyl-2,5-dichlorohexane (5,054 g), mp 67°–69° C.

STEP B. 2,5-Dimethyl-2,5-dichlorohexane (183 g, 1 mol) was stirred with m-cresol (129.6 g, 1.2 mol) and aluminum chloride (4 g) was added in one direction. The mixture was heated at 95° C., with stirring for 1.5 h, after which ethylene dichloride (100 mL) was added and then the heating was continued. After 1 h the mixture was cooled to 20° C. and poured onto an ice-water/hydrochloric acid mixture (150 mL, 10% HCl solution). The mixture was then extracted with toluene (500 mL). The organic layer was separated, washed with brine (3×50 mL) and dried ($Na_2SO_4$). The solvent was removed by distillation and the residue was crystallized from a hexane/benzene solvent mixture to give 1-hydroxy-3,5,5,8,8-pentamethyl-5,6,7,8-tetrahydronaphthalene (171 g), mp 133°–134° C., GLC purity 99%+. $^1$H-NMR (CDCl$_3$) δ 6.82 (1H, broad s), 6.35 (1H, d, J=1.4 Hz), 4.72 (1H, s), 2.30 (3H, s), 1.71 (4H, m), 1.49 (6H, s), 1.34 (6H, s). $^{13}$C-NMR (CDCl$_3$) δ 154.2 (1C, s), 147.8 (1C, s), 135.7 (1C, s), 128.0 (1C, s), 120.2 (1C, d), 114.6 (1C, d), 37.9 (1C, t), 35.2 (1C, t), 34.6 (1C, s), 33.7 (1C, s), 32.0 (2C, q), 28.5 (2C, q), 20.8 (1C, q). IR (KBr) 3,503 cm$^{-1}$, MS (m/e) 218 (M+, 24.7), 203 (100.0), 161 (55.1), 147 (23.9), 57 (10.9).

EXAMPLE 2

This example illustrates the preparation of 2-formyl-1-methoxy-3,5,5,8,8-pentamethyl-5,6,7,8-tetrahydronaphthalene (3a) according to Process I.

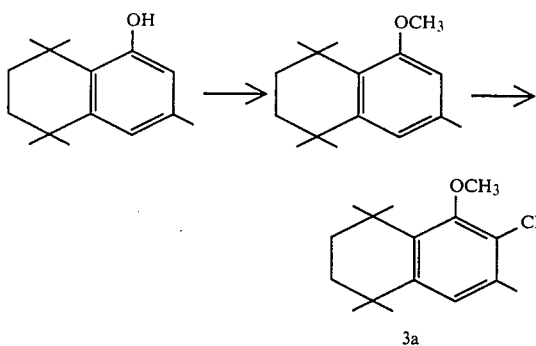

(a) Methylation. A solution of sodium hydroxide (38 g, 0.95 mol) in water (1 L) was added to a mixture of 1-hydroxy-3,5,5,8,8-pentamethyl-5,6,7,8-tetrahydronaphthalene (109 g, 0.5 mol), dimethyl sulfate (126 g, 1 mol) and Adogen 464* (21.6 g) in methylene dichloride (2 L). The reaction mixture was stirred vigorously at 25°–28° C. for 1 h, after which the organic layer was separated, combined with ammonium hydroxide solution (500 mL, 10%), and stirred vigorously at 20°–25° C. for 0.5 h. The organic layer was then separated and the washing procedure repeated, after which the organic layer was separated, washed with water (2×100 mL), then with brine (50 mL), and dried (Na$_2$SO$_4$). The solvent was removed by distillation and the residue was crystallized from hexane yielding 1-methoxy-3,5,5,8,8-pentamethyl-5,6,7,8-tetrahydronaphthalene (95 g), mp 49°–50° C., GLC purity 99%+. $^1$H-NMR (CDCl$_3$) δ6.89 (1H, d, J=1.4 Hz), 6.63 (1H, d, J=1.4 Hz), 3.89 (3H, s), 2.41 (3H, s), 1.74 (4H, m), 1.48 (6H, s), 1.38 (6H, s). IR (KBr) 1273, 1257 cm$^{-1}$, MS (m/e) 232 (M$^+$, 16.9), 217 (100.0), 175.3 (19.6), 218.6 (16.0).

*Methyltrialkyl (C$_8$–C$_{10}$) ammonium chloride (b) Formylation. 1-Methoxy-3,5,5,8,8-pentamethyl-5,6,7,8-tetrahydronaphthalene (50 g, 0.2155 mol) was added to a stirred mixture of hexamethylenetetramine (31.4 g, 0.224 mol) and trifluoroacetic acid (250 mL) at 35°–40° C., under a nitrogen atmosphere. The stirred reaction mixture was heated to 85°–90° C. and maintained at this temperature for 1.5 h. Trifluoroacetic acid was removed by distillation and the residue was poured onto an ice-water mixture (800 mL). The mixture was then stirred for 0.5 h, neutralized with a 10% sodium carbonate solution, and the product extracted with benzene (2×150 mL). The combined extracts were washed with brine (50 mL) and dried (Na$_2$SO$_4$). The solvent was then removed by distillation and the residue crystallized from hexane to provide 2-formyl-1-methoxy-3,5,5,8,8-pentamethyl-5,6,7,8-tetrahydronaphthalene (14 g), mp 78° C. GLC purity 100%. $^1$H-NMR (CDCl$_3$) δ10.39 (1H, s), 6.93 (1H, s), 3.86 (3H, s), 2.49 (3H, s), 1.63 (4H, s), 1.39 (6H, s), 1.37 (6H, s). $^{13}$C-NMR (CDCl$_3$) δ192.1 (1C, d), 165.4 (1C, s), 153.5 (1C, s), 138.3 (1C, s), 135.8 (1C, s), 125.8 (2C, s, d), 66.1 (1C, q) 38.1 (1C, t), 35.3 (1C, s), 34.8 (1C, t), 34.3 (1C, s), 31.7 (2C, q), 29.8 (2C, q), 20.8 (1C, q). IR (melt) 1245, 1682 cm$^{-1}$, MS (m/e) 260 (M$^+$, 20.8), 246 (18.7), 245 (100.0), 141 (12.3), 128 (13.2), 115 (13.0).

EXAMPLE 3

This example illustrates another formylation procedure that can be used in the preparation of 2-formyl-1-methoxy-3,5,5,8,8-pentamethyl-5,6,7,8-tetrahydronaphthalene (3a) according to Process I.

1-Methoxy-3,5,5,8,8-pentamethyl-5,6,7,8-tetrahydronaphthalene (23.2 g, 0.1 mol), prepared according to Example 2, was added to a stirred solution of acetic acid (18.2 g, 0.3 mol), 85% phosphoric acid (17.6 g, 0.15 mol), hydrochloric acid (28.7 g, 0.3 mol) and paraformaldehyde (7.3 g, 0.24 mol). The mixture was stirred and heated at 95° C. for 16 h. The reaction mixture was then cooled to 25° C., benzene (50 mL) added, and stirred vigorously. The organic layer was separated, washed with water (2×25 mL), neutralized with 5% sodium bicarbonate solution, and dried (Na$_2$SO$_4$). The solvent was removed by distillation to provide 2-chloromethyl-1-methoxy-3,5,5,8,8,-pentamethyl-5,6,7,8-tetrahydronaphthalene, GLC purity 84%.

Sodium (2.87 g, 0.125 mol) was added in small pieces to methanol (40 mL) during 0.5 h at 25°–45° C., then nitropropane (13.35 g, 0.15 mol) was added. The mixture was heated with stirring at 65° C. during 0.25 h, then a slurry of 1-methoxy-2-chloromethyl-3,5,5,8,8-pentamethyl-5,6,7,8-tetrahydronaphthalene (28 g, 0.1 mol) in methanol (50 mL) was added, in portions, during 0.25 h, at 65° C. The stirred mixture was heated at 65°–68° C. for 2.5 h, after which excess methanol was removed by distillation. The residue was dissolved in benzene (100 mL) and the solution washed with water (3×25 mL), then with brine (25 mL) and dried (Na$_2$SO$_4$). The solvent was evaporated and the residue distilled to yield 18 g of material, (bp 116°–124° 1 C./0.4 mm), which crystallized from hexane to provide 2-formyl-1-methoxy-3,5,5,8,8-pentamethyl-5,6,7,8-tetrahydronaphthalene (3a), mp 78°–78.5° C. exhibiting the expected spectral data.

EXAMPLE 4

This example illustrates both the preparation of 2-formyl-1-hydroxy-3,5,5,8,8-pentamethyl-5,6,7,8-tetrahydronaphthalene (4a) and 2-formyl-1-methoxy-3,5,5,8,8-pentamethyl-5,6,7,8-tetrahydronaphthalene (3a) according to Process II.

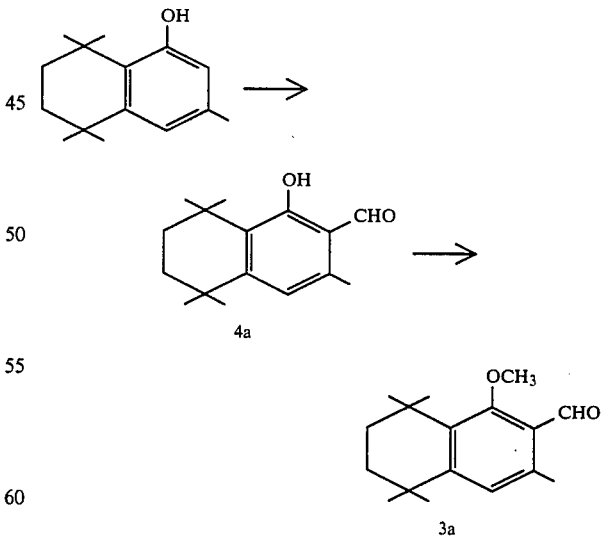

(a) Formylation. Hexamethylenetetramine (21 g, 0.15 mol) and 1-hydroxy-3,5,5,8,8-pentamethyl-5,6,7,8-tetrahydronaphthalene were added in one portion with stirring to acetic acid (250 mL) and the mixture was heated at 95°–100° C. for 2 h. After cooling to 80°–85° C., water (250 mL) and concentrated hydrochloric acid (60 mL) were added and the mixture was heated at 95°-100° C. for a further 2 h. The reaction product was then cooled to 20° C., diethyl ether (150 mL) was added and the mixture was stirred vigorously. The organic layer was separated, washed with brine (2×50 mL), neutralized with 5% sodium bicarbonate solution (100 mL), and dried (Na₂SO₄). The solvent was removed by distillation and the residue was distilled to yield 2-formyl-1-hydroxy-3,5,5,8,8-pentamethyl-5,6,7,8-tetrahydronaphthalene (4a) (18 g), mp 91°-92° C., GLC purity 99%+. $^1$H-NMR (CDCl₃) δ12.92 (1H, s), 10.21 (1H, s), 6.73 (1H, s), 1.68 (3H, s), 1.67 (4H, s), 1.48 (6H, s), 1.32 (6H, s). $^{13}$C-NMR (CDCl₃) δ194.4 (1C, d), 163.5 (1C, s), 156.5 (1C, s), 138.0 (1C, s), 130.8 (1C, s), 120.1 (1C, d), 116.2 (1C, s), 37.7 (1C, t), 35.3 (1C, s), 34.6 (1C, t), 33.9 (1C, s), 31.0 (2C, q), 27.7 (2C, q), 17.8 (1C, q). IR (KBr) 1615, 1628 cm$^{-1}$, MS (m/e) 246.2 (M+, 23.9) 231.2 (100.0), 189.1 (19.9), 161.2 (19.2).

(b) Methylation. A solution of sodium hydroxide (0.98 g, 0.0244 mol) in water (24 mL) was added in one portion to a solution of 2-formyl-1-hydroxy-3,5,5,8,8-pentamethyl-5,6,7,8-tetrahydronaphthalene (3 g, 0.0122 mol), dimethyl sulfate (3.07 g, 0.0244 mol) and Adogen 464* (0.56 g) in methylene dichloride (48 mL). The mixture was stirred vigorously at 38°-40° C. for 4 h. After cooling, the organic layer was separated, washed with brine (3×20 mL) and dried (Na₂SO₄). The solvent was removed by distillation and the residue was distilled to yield 2-formyl-1-methoxy-3,5,5,8,8-pentamethyl-5,6,7,8-tetrahydronaphthalene (3a), (2.5 g), mp 78° C. (from hexane), GLC purity 99.7%, exhibiting the expected spectral data.

*Methyltrialkyl (C₈-C₁₀) ammonium chloride

EXAMPLE 5

This example illustrates the preparation of a starting material, 1-hydroxy-4,5,5,8,8-pentamethyl-5,6,7,8-tetrahydronaphthalene

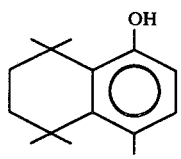

Employing procedures and materials similar to those described in Example 1, except that p-cresol was substituted for m-cresol, and the reaction was carried out in the presence of petroleum ether (bp 55°-100° C.) as solvent, there was obtained the desired product, 1-hydroxy-4,5,5,8,8-pentamethyl-5,6,7,8-tetrahydronaphthalene, 43% theor., GLC purity 98%, exhibiting the expected spectral data.

EXAMPLE 6

This example illustrates both the preparation of 2-formyl-1-hydroxy-4,5,5,8,8-pentamethyl-5,6,7,8-tetrahydronaphthalene and 2-formyl-1-methoxy-4,5,5,8,8,-pentamethyl-5,6,7,8-tetrahydronaphthalene (3b) according to Process II:

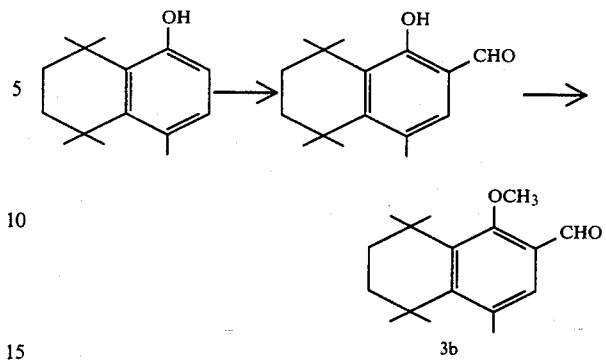

(a) Formylation. 1-Hydroxy-4,5,5,8,8-pentamethyl-5,6,7,8-tetrahydronaphthalene (78 g, 0.358 mol) was stirred with glacial acetic acid (632 mL) and hexamethylenetetramine (93.6 g, 0.669 mol). The mixture was heated at 105°-110° C. for 10 h. Hot water (632 mL) was added and the heating was continued for an additional 2.5 h at 100° C. The mixture was cooled to 20° C., toluene (250 mL) was added, and the mixture was stirred vigorously. The organic layer was separated, washed with water (2×50 mL), then neutralized with 5% NaHCO₃ solution, and finally washed with brine (50 mL). The solvent was removed by distillation and the residue distilled to yield 2-formyl-1-hydroxy-4,5,5,8,8-pentamethyl-5,6,7,8-tetrahydronaphthalene (45 g), bp 138°-146° C./1 mm, GLC purity 95%. $^1$H-NMR (CDCl₃) δ11.63 (1H, s), 9.73 (1H, s), 7.09 (1H, s), 2.52 (3H, s), 1.66 (3H, s), 1.47 (6H, s), 1.42 (6H, s). $^{13}$C-NMR (CDCl₃) δ196 (1C, d), 159 (1C, s), 155 (1C, s), 134.7 (1C, d), 134.1 (1C, s), 128 (1C, s), 118.1 (1C, s), 39.3 (1C, t), 37.8 (1C, t), 36.5 (1C, s), 35.2 (1C, s), 28.7 (2C, q), 27.9 (2C, q), 23.5 (1C, q). IR (KBr) 1637 cm$^{-1}$, MS (m/e) 246.2 (M+, 36.1), 231.2 (100.0), 161.2 (41.6), 189.1 (27.9).

(b) Methylation. 2-Formyl-1-hydroxy-4,5,5,8,8-pentamethyl-5,6,7,8-tetrahydronaphthalene (42 g, 0.17 mol) was stirred with toluene (656 mL), and potassium hydroxide 85% (16.8 g, 0.255 mol) was added in one portion. The mixture was heated to 40° C., dimethyl sulfate (32.13 g, 0.255 mol) added at 40°-45° C. during 0.5 h, and the heating continued at 50° C. for an additional 1.5 h. The mixture was cooled to 20° C., neutralized with 5% HCl solution, then washed with water (20 mL), and finally washed with brine (25 mL). The solvent was removed by distillation and the residue distilled to give 2-formyl-1-methoxy-4,5,5,8,8-pentamethyl-5,6,7,8-tetrahydronaphthalene (36 g), bp 140°-142° C./1.5 mm, GLC purity 95%. Crystallization from hexane gave 28 g material, GLC purity 99%. $^1$H-NMR (CDCl₃) δ10.23 (2H, s), 7.41 (1H, s), 3.89 (3H, s), 2.52 (3H, s), 1.63 (4H, s), 1.42 (6H, s), 1.40 (6H, s). $^{13}$C-NMR (CDCl₃) δ189.9 (1C, d), 162.3 (1C, s), 153.1 (1C, s), 139.9 (1C, s), 132.7 (1C, s), 131.3 (1C, d), 126.5 (1C, s), 66.0 (1C, q), 39.4 (1C, t), 38.2 (1C, t), 36.4 (1C, s), 35.6 (1C, s), 30.0 (2C, q), 28.9 (2C, q), 23.7 (1C, q). IR (KBr) 1683, 1235 cm$^{-1}$, MS (m/e) 260.3 (M+, 46.3), 245.2 (100.0), 175 (38.5), 128 (31.1).

EXAMPLE 7

This example illustrates the preparation of a starting material, 3-ethyl-1-hydroxy-5,5,8,8-tetramethyl-5,6,7,8-tetrahydronaphthalene

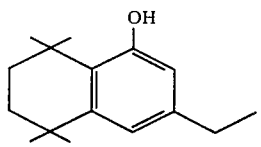

Employing procedures and materials similar to those described in Example 1, except that 3-ethylphenol was substituted for m-cresol, and the reaction was carried out in the presence of ethylene dichloride as solvent, there was obtained the desired product, 3-ethyl-1-hydroxy-5,5,8,8-tetramethyl-5,6,7,8-tetrahydronaphthalene 66% theor., GLC purity 99%+, exhibiting the expected spectral data.

EXAMPLE 8

This example illustrates both the preparation of 3-ethyl-2-formyl-1-hydroxy-5,5,8,8-tetramethyl-5,6,7,8-tetrahydronaphthalene and 3-ethyl-2-formyl-1-methoxy-5,5,8,8-tetramethyl-5,6,7,8-tetrahydronaphthalene (3c) according to Process II:

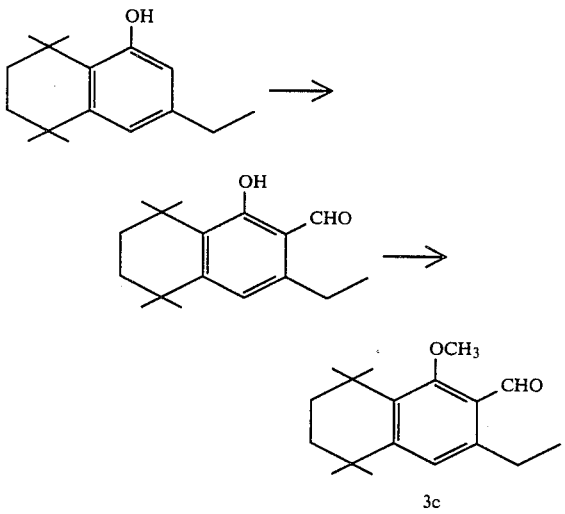

(a) Formylation. 3-Ethyl-1-hydroxy-5,5,8,8-tetramethyl-5,6,7,8-tetrahydronaphthalene (94 g, 0.405 mol) was stirred with glacial acetic acid (670 mL), and hexamethylenetetramine (102.6 g, 0.73 mol) was added in one portion. The mixture was heated at 95° C. for 3 h, hot water (670 mL) added, and the heating was continued for an additional 1.5 h at 100° C. The mixture was cooled to 20° C., toluene (200 mL) was added, and the mixture was stirred vigorously. The organic layer was separated, washed with water (3×150 mL), then neutralized with 5% NaHCO₃ solution, and finally washed with brine (50 mL). The solvent was evaporated and the residue distilled to give 3-ethyl-2-formyl-1-hydroxy-5,5,8,8-tetramethyl-5,6,7,8-tetrahydronaphthalene (77.9 g), bp 127°–132° C./0.5 mm, GLC purity 98%, $^1$H-NMR (CDCl₃) δ12.87 (1H, s), 10.20 (1H, s), 6.72 (1H, s), 2.89 (2H, q), 1.65 (4H, m), 1.44 (6H, s), 1.30 (3H, t), 1.29 (6H, s). $^{13}$C-NMR (CDCl₃) δ194.3 (1C, d), 163.6 (1C, s), 156.7 (1C, s), 144.6 (1C, s), 130.8 (1C, s), 118.5 (1C, d), 115.2 (1C, s), 37.7 (1C, t), 35.5 (1C, s), 34.7 (1C, t), 34.0 (1C, s), 31.1 (2C, q), 27.7 (2C, q), 24.8 (1C, t), 16.9 (1C, q). IR (KBr) 1609 cm$^{-1}$ MS (m/e) 260.3 (M+, 22.6), 245.2 (100.0), 203.3 (18.2), 246.2 (17.0).

(b) Methylation. 3-Ethyl-2-formyl-1-hydroxy-5,5,8,8-tetramethyl-5,6,7,8-tetrahydronaphthalene (48.2 g, 0.185 mol) was stirred with toluene (650 mL), and potassium hydroxide 85% (19.5 g, 0.296 mol) was added in one portion. The mixture was heated to 45° C. and dimethyl sulfate (35 g, 0.278 mol) was added during 0.5 h at 45°–50° C. The heating was continued for an additional 0.5 h at 50° C. The mixture was cooled to 20° C., neutralized with 5% hydrochloric acid, washed with water (50 mL), and then finally washed with brine (30 mL). Solvent was removed by distillation and the residue distilled to give 3-ethyl-2-formyl-1-methoxy-5,5,8,8-tetramethyl-5,6,7,8-tetrahydronaphthalene (40.6 g), GLC purity 98%. Crystallization from hexane gave 27 g material, GLC purity 99%. $^1$H-NMR (CDCl₃) δ10.38 (1H, s), 6.97 (1H, s), 3.85 (3H, s), 2.89 (2H, q), 1.64 (4H, s), 1.40 (6H, s), 1.28 (6H, s), 1.20 (3H, t). $^{13}$C-NMR (CDCl₃) δ192.0 (1C, d), 165.3 (1C, s), 153.6 (1C, s), 144.4 (1C, s), 135.7 (1C, s), 125.3 (1C, s), 124.1 (1C, d), 66.0 (1C, q), 38.1 (1C, t), 35.4 (1C, s), 34.8 (1C, t), 34.3 (1C, s), 31.8 (2C, q), 29.8 (2C, q), 26.6 (1C, t), 15.7 (1C, q). IR (KBr) 1275, 1263 cm$^{-1}$, MS (M/e) 274.2 (M+, 17.1), 258.1 (100.0), 260.3 (20.3), 128.1 (15.1).

EXAMPLE 9

This example illustrates the preparation of a starting material, 1-hydroxy-3,4,5,5,8,8-hexamethyl-5,6,7,8-tetrahydronaphthalene

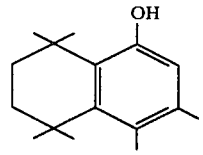

Employing procedures and materials similar to those described in Example 1, except that 3,4-dimethylphenol was substituted for m-cresol, and the reaction was carried out in the presence of ethylene dichloride as solvent, there was obtained 1-hydroxy-3,4,5,5,8,8-hexamethyl-5,6,7,8-tetrahydronaphthalene, 15% theor., GLC purity 100%, exhibiting the expected spectral data.

EXAMPLE 10

This example illustrates the preparation of 2-formyl-1-hydroxy-3,4,5,5,8,8-hexamethyl-5,6,7,8-tetrahydronaphthalene and 2-formyl-1-methoxy-3,4,5,5,8,8-hexamethyl-5,6,7,8-tetrahydronaphthalene (3d) according to Process II:

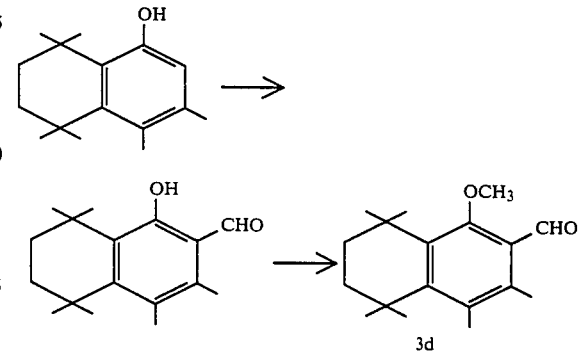

(a) Formylation. 1-Hydroxy-3,4,5,5,8,8-hexamethyl-5,6,7,8-tetrahydronaphthalene (15 g, 0.0646 mol) was stirred with glacial acetic acid (100 mL), and hexamethylenetetramine (15 g, 0.107 mol) was added in one portion. The mixture was heated at 100° C. for 2 h. Hot water (100 mL) was added and the heating continued for an additional 0.5 h at 100° C. The mixture was cooled to 20° C., toluene (25 mL) was added, and the mixture was stirred vigorously. The organic layer was separated, washed with water (2×10 mL), then neutralized with 5% NaHCO$_3$ solution and finally washed with brine (10 mL). The solvent was removed by distillation, and the residue crystallized from hexane, to give 2-formyl-1-hydroxy-3,4,5,5,8,8-hexamethyl-5,6,7,8-tetrahydronaphthalene (8.8 g), GLC purity 94%. $^1$H-NMR (CDCl$_3$) δ12.94 (1H, s), 10.36 (1H, s), 2.43 (3H, s), 2.36 (3H, s), 1.65 (4H, s), 1.48 (6H, s), 1.46 (6H, s). $^{13}$C-NMR (CDCl$_3$) δ195.4 (1C, d), 161.4 (1C, s), 156.0 (1C, s), 138.0 (1C, s), 131.9 (1C, s), 126.6 (1C, s), 116.7 (1C, s), 40.2 (1C, t), 37.9 (1C, t), 36.5 (1C, s), 35.1 (1C, s), 29.5 (2C, q), 28.1 (2C, q), 19.3 (1C, q), 14.1 (1C, q). IR (KBr) 1628 cm$^{-1}$, MS (m/e) 260.3 (M+, 38.6), 245.2 (100.0), 175.1 (28.7), 189.1 (20.1).

(b) Methylation. 2-Formyl-1-hydroxy-3,4,5,5,8,8-hexamethyl-5,6,7,8-tetrahydronaphthalene (8.7 g, 0.0335 mol) was stirred with toluene (60 mL), and potassium hydroxide 85% (3.1 g, 0.047 mol) was added in one portion. The mixture was heated to 55° C., dimethyl sulfate (6.3 g, 0.05 mol) added during 0.5 h at 55°–60° C., and the heating continued at 55°–60° C. for 4 h. The mixture was cooled to 20° C., neutralized with 5% hydrochloric acid, then washed with water (10 mL), and finally washed with brine (10 mL). The solvent was removed by distillation and the residue distilled to give 2-formyl-1-methoxy-3,4,5,5,8,8-hexamethyl-5,6,7,8-tetrahydronaphthalene (5.8 g), GLC purity 97%. Crystallization from hexane gave 3.5 g material with GLC purity 100%. $^1$H-NMR (CDCl$_3$) δ10.40 (1H, s), 3.78 (3H, s), 2.40 (3H, s), 2.37 (3H, s), 1.64 (4H, s), 1.45 (6H, s), 1.42 (6H, s). $^{13}$C-NMR (CDCl$_3$) δ193.5 (1C, d), 162.9 (1C, s), 151.6 (1C, s), 137.7 (1C, s), 136.7 (1C, s), 132.5 (1C, s), 126.9 (1C, s), 65.7 (1C, q), 40.3 (1C, t), 38.2 (1C, t), 36.2 (1C, s), 35.2 (1C, s), 30.2 (2C, q), 29.8 (2C, q), 19.7 (1C, q), 15.8 (1C, q). IR (KBr) 1244, 1271, 1682 cm$^{-1}$, MS (m/e) 274.2 (M+, 34.9), 259.1 (100.0), 260.2 (21.7), 189.1 (21.5).

EXAMPLE 11

Floral Aldehydic Perfume Composition

Classic floral aldehydic compositions were prepared by mixing the following ingredients:

| Ingredients | Parts by Weight |
|---|---|
| Oil Ylang | 100 |
| Dimethyl-α-ionone | 110 |
| Rose de Mai Absolute at 10%* | 60 |
| Oil Patchouly Rectified | 10 |
| Oil Sandalwood | 10 |
| Oil Vetiver Reunion | 10 |
| Hydroxy Citronellal | 80 |
| Oil Clove | 15 |
| Ethyl Vanillin at 10%* | 30 |
| Vanillin at 10%* | 20 |
| Coumarin | 85 |
| Aldehyde C-10 at 10%* | 40 |
| Aldehyde C-11 Undecylenic at 10%* | 40 |
| Aldehyde C-12 Lauric at 10%* | 40 |
| Oil Bois de Rose Brazilian | 20 |
| Linalyl Acetate | 10 |
| Essence Styrax | 15 |
| Oakmoss Absolute at 50%* | 20 |
| Mousse de Metra at 10%* | 30 |
| α-Irone at 10%* | 10 |
| Jasmin Absolute at 10%* | 150 |
| Tincture Vanilla | 40 |
| Aldehyde C-14 at 10%* | 5 |
| Oil Rose Turkish at 10%* | 15 |
| Linalool from Bois de Rose | 35 |
| Total | 1000 |

*In odorless diethyl phthalate.

When 150 parts of the novel Compound 3a were added to 1000 parts of the above mixture, a floral aldehydic type composition having a richer, fuller, and more tenacious odor was obtained.

When 150 parts of a mixture of musk compounds, comprising 70 parts of Musk Ambrette, 50 parts of Musk Ketone, and 30 parts of Musk Xylene were added to 1000 parts of the above mixture, a floral aldehydic type composition having substantially similar organoleptic properties to the floral aldehydic type composition prepared with the novel Compound 3a resulted. The novel musk chemical 3a can therefore be used in nitro-musk formulations in place of known musk chemicals to achieve very similar organoleptic effects.

EXAMPLE 12

Perfume Composition of the Fougere Type

Fougere type compositions were prepared by mixing the following ingredients:

| Ingredients | Parts by Weight |
|---|---|
| Citronellol | 10 |
| Dimethyl-α-ionone | 10 |
| Geranyl Acetate | 10 |
| Oil Labdanum Cistus at 10%* | 10 |
| Oil Clove | 10 |
| Labdanum Colorless at 10%* | 30 |
| Benzyl Salicylate | 20 |
| Oil Petitgrain Terpeneless | 20 |
| Oil Orange Bitter | 20 |
| Isoamyl Salicylate | 30 |
| Coumarin | 30 |
| Geraniol | 30 |
| Oil Patchouly | 30 |
| Oil Lavandin Grosso | 50 |
| Oil Lavender Barreme at 38–42% | 60 |
| Oakmoss Absolute at 50%* | 100 |
| Oil Bergamot | 250 |
| Total | 720 |

*In odorless diethyl phthalate.

When 120 parts of novel musk Compound 3a were added to 720 parts of the above mixture, a Fougere type composition having a warmer, animal, musky quality, with greater tenacity than the basic composition was obtained.

When 120 parts of a mixture of musk compounds comprising 60 parts of Musk Ambrette, 40 parts of Musk Ketone and 20 parts of Musk Xylene were added to 720 parts of the above mixture, a Fougere type composition having substantially similar organoleptic properties to that of the Fougere type composition prepared with the novel Compound 3a resulted. Novel musk chemical 3a can therefore be used in nitro-musk formulations in place of known musk chemicals to achieve very similar organoleptic effects.

EXAMPLE 13

Perfume Composition of the Oriental Bouquet Type

Oriental bouquet compositions were prepared by mixing the following ingredients:

| Ingredients | Parts by Weight |
| --- | --- |
| Aldehyde C-12 at 10%* | 5 |
| Phenyl Ethyl Acetate | 5 |
| Indole at 10%* | 5 |
| Aldehyde C-11 Undecylenic at 10%* | 10 |
| Oil Vetiver Haiti | 10 |
| Amyl Cinnamic Aldehyde | 15 |
| Oil Sandalwood E.I. | 20 |
| Vanillin | 20 |
| Tolu Balsam at 50%* | 20 |
| Hexyl Cinnamic Aldehyde | 25 |
| Oil Patchouly | 30 |
| Benzoin Siam Resinoid at 50%* | 40 |
| Oil Petitgrain Paraguay | 50 |
| Heliotropin | 50 |
| Citronellol | 60 |
| Benzyl Acetate Extra | 75 |
| Phenyl Ethyl Alcohol | 200 |
| Oil Bergamot Reconstituted | 210 |
| Total | 850 |

*In odorless diethyl phthalate.

When 150 parts of the novel Compound 3c were added to 750 parts of the above mixture, an oriental bouquet tyype composition having a warm, sweet, voluminous musky character was obtained.

When 150 parts of a mixture of nitro-musk compounds, comprising 40 parts of Musk Xylene, 50 parts of Musk Ketone and 60 parts of Musk Ambrette were added to 750 parts of the above mixture, an oriental bouquet type composition having substantially similar organoleptic properties to the oriental bouquet type composition prepared with novel Compound 3c resulted. The novel musk Compound 3c can therefore be used in nitro-musk formulations in place of known musk chemicals to achieve very similar organoleptic effects.

EXAMPLE 14

Preparation of a Soap Compositions

A total of 300 g of soap chips, produced from unperfumed sodium base toilet soap, made of tallow and coconut oil, were mixed with 30 g of a 10% ethyl alcohol solution of Compound 3a or Compound 3c, until substantially homogenous compositions were obtained. The soap composition containing Compound 3a manifested an excellent musk aroma, sweet and exalting with the character of the macrocyclic musks. The soap composition containing Compound 3c manifested a long-lasting, sweet, slightly woody, musky odor.

EXAMPLE 15

Preparation of a Solid Detergent Compositions

A total of 100 g of a high temperature detergent powder, as sold under the trademark ORVUS, was mixed with 2 g of a 10% ethyl alcohol solution of Compound 3a or Compound 3c, until substantially homogenous compositions were obtained. The detergent composition containing Compound 3a manifested an excellent musk aroma, sweet and exalting, with the character of the macrocyclic musks. The detergent composition containing Compound 3c manifested a long-lasting, sweet, slight woody, musky odor.

As will be apparent to those skilled in the art, in the light of the foregoing disclosure, many alterations, modifications, substitutions and combinations are possible in the practice of this invention without departing from the spirit or scope thereof.

What is claimed is:

1. The process of preparing compounds having the structure:

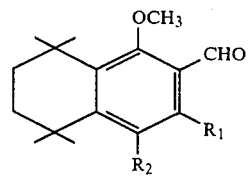

wherein $R_1$ and $R_2$ are hydrogen, methyl, or ethyl, which comprises:

a. methylating compounds having the structure:

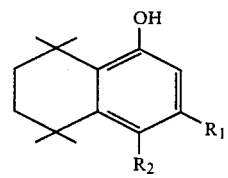

wherein $R_1$ and $R_2$ are hydrogen, methyl, or ethyl to produce methoxy derivatives having the structure:

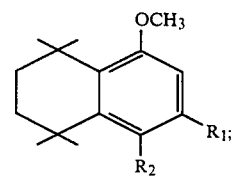

b. formylating the methoxy derivatives to prepare compounds having the structure:

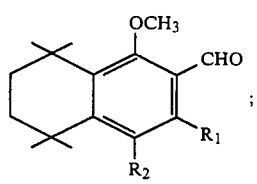

and c. recovering said compounds.

2. The process of preparing compounds having the structure:

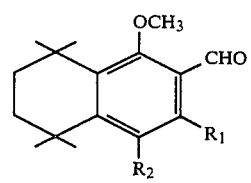

wherein $R_1$ and $R_2$ are hydrogen, methyl, or ethyl, which comprises:

a. formylating compounds having the structure:

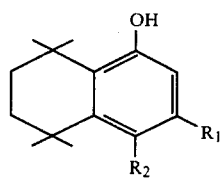

wherein R₁ and R₂ are hydrogen, methyl, or ethyl to produce aldehyde derivatives having the structure:

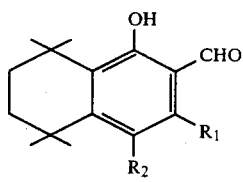

b. methylating the aldehyde derivatives to prepare compounds having the structure:

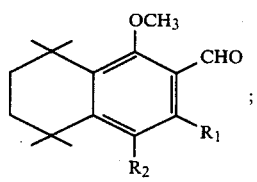

and c. recovering said compounds.

3. The process of preparing compounds having the structure:

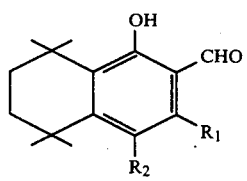

wherein R₁ and R₂ are hydrogen, methyl, or ethyl which comprises:

a. formylating compounds having the structure:

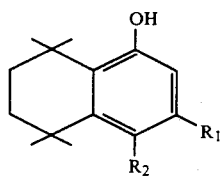

wherein R₁ and R₂ are hydrogen, methyl, or ethyl to produce compounds having the structure:

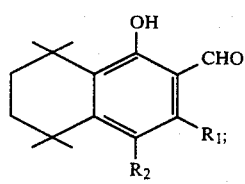

and b. recovering said compounds.

4. A method in accordance with claim 1 wherein said compounds are methylated in a reaction mixture employing dimethylsulfate.

5. A method in accordance with claim 1 wherein said methoxy derivatives are formylated in a reaction mixture employing an acetic acid and hexamethylenetetramine or paraformaldehyde.

6. A method in accordance with claim 1 wherein said compounds are methylated in a reaction mixture employing dimethylsulfate and wherein said methoxy derivatives arenformylated in a reaction mixture employing an acetic acid and hexamethylenetetramine or paraformaldehyde.

7. A method in accordance with claim 2 wherein said compounds are formylated in a reaction mixture containing acetic acid and hexamethylenetetramine or paraformaldehyde wherein said aldehyde derivatives are methylated in a reaction mixture containing dimethylsulfate.

8. A method in accordance with claim 2 wherein said compounds are formylated in a reaction mixture containing acetic acid and hexamethylenetetramine or paraformaldehyde.

9. A method in accordance with claim 2 wherein said aldehyde derivatives are methylated in a reaction mixture containing dimethylsulfate.

10. A method in accordance with claim 3 wherein said compounds are formylated in a reaction mixture containing an acetic acid and hexamethylenetetramine and paraformaldehyde.

* * * * *